(12) United States Patent
Mers Kelly et al.

(10) Patent No.: US 6,283,979 B1
(45) Date of Patent: *Sep. 4, 2001

(54) SUTURING DEVICE WITH TENSIONING ADJUSTMENT MEMBER

(76) Inventors: William Charles Mers Kelly, 5420 Foxwood Dr., Crestwood, KY (US) 40014; David Young Phelps, 904 Shady La., Louisville, KY (US) 40223; Bryan Patrick Kiple, 21524 W. Maurine Dr., Lake Villa, IL (US) 60046

(*) Notice: Subject to any disclaimer, the term of this patent is extended or adjusted under 35 U.S.C. 154(b) by 0 days.

This patent is subject to a terminal disclaimer.

(21) Appl. No.: 09/349,218
(22) Filed: Jul. 6, 1999

Related U.S. Application Data

(63) Continuation of application No. 09/006,736, filed on Jan. 14, 1998, now Pat. No. 5,919,199.

(51) Int. Cl.[7] .................................................. A61B 17/10
(52) U.S. Cl. .................................................. 606/139; 606/222
(58) Field of Search .................................. 606/139, 144, 606/222, 148, 146; 289/17

(56) References Cited

U.S. PATENT DOCUMENTS

| 2,579,192 | * | 12/1951 | Kohl | 606/139 |
| 5,350,385 | * | 9/1994 | Christy | 606/139 |
| 5,919,199 | * | 7/1999 | Mers Kelly | 606/139 |

* cited by examiner

Primary Examiner—Henry J. Recla
Assistant Examiner—Lien Ngo
(74) Attorney, Agent, or Firm—Don Halgren

(57) ABSTRACT

The present invention includes a method of suturing a body part by the use of an elongated articulable suture device comprising the steps of: providing a handle having a proximal end and a distal end; attaching an elongated, articulable suture needle at the distal end of said handle; placing a movable sheath about the suture needle; threading a tensionable member through the suture needle from a proximal to distal path and back again through a distal to proximal path, one end of the tensional member being fixed to the handle, and a second end of the tensional member being attached to a tension adjusting member; placing a suture thread in a holder in said distalmost end of the suture and threading a body part by movement of the suture needle about a body part.

7 Claims, 6 Drawing Sheets

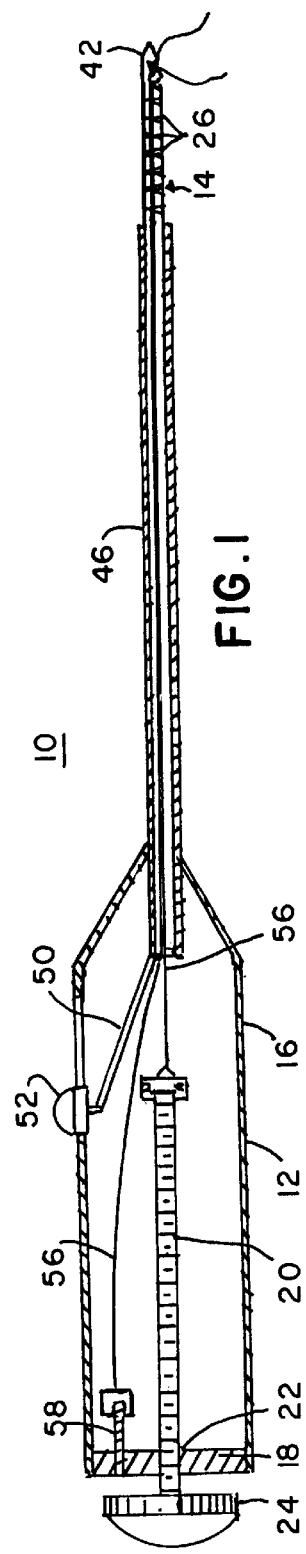
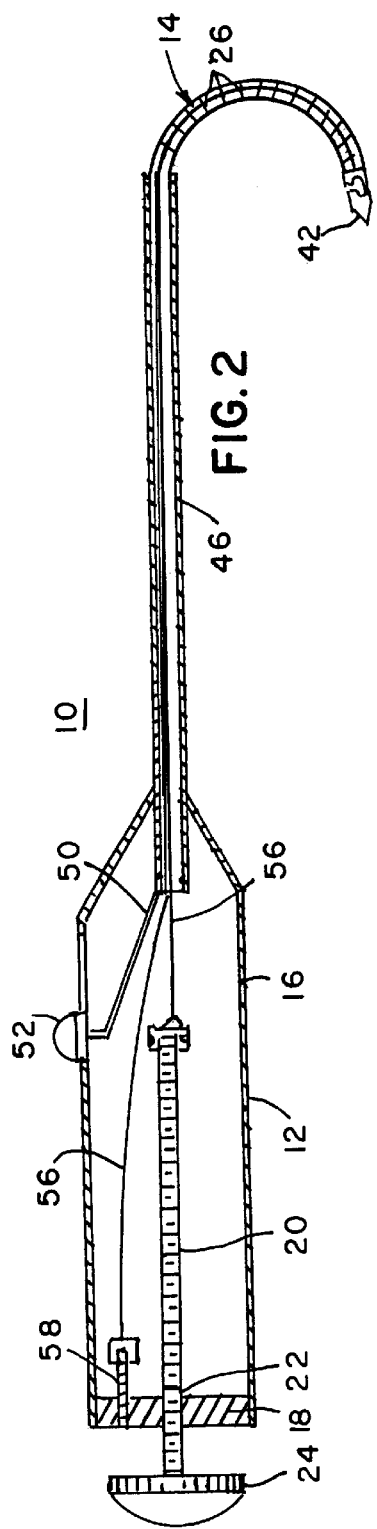
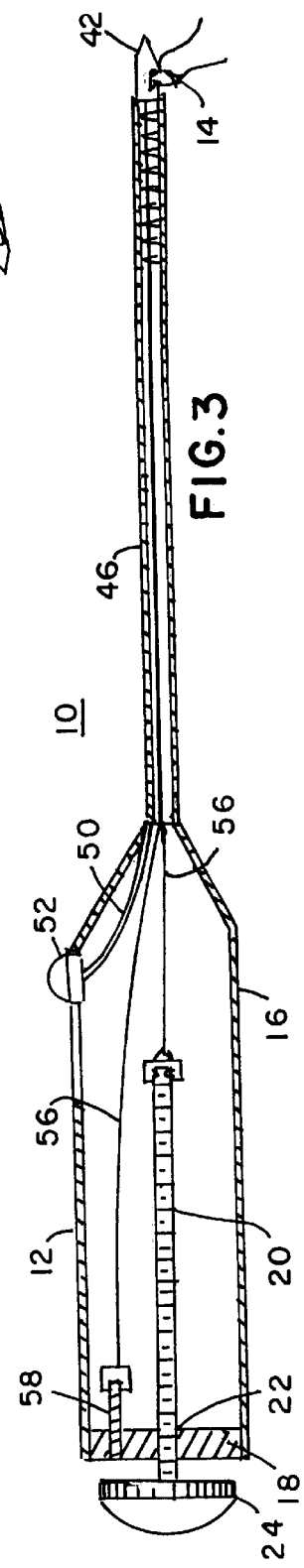

SUTURING DEVICE WITH TENSIONING ADJUSTMENT MEMBER

This is a continuation of U.S. patent application Ser. No. 09/006,736 filed Jan. 14, 1998; now U.S. Pat. No. 5,919,199.

BACKGROUND OF THE INVENTION

1. Field of the Invention

This invention relates to medical devices, and more particularly to an articulable suturing needle for use in internal body stitching requirements.

2. Prior Art

Suturing is an art common in the medical field. Typically, suturing is done with some form of needle or thread, and sometimes it is replaced with a staple arrangement. Advanced medical techniques utilizing laproscopy have thus permitted surgical techniques to be accomplished on a body, through minor openings within the body surface. After surgery has been completed under a laproscopic technique, suturing is necessary. A needle held in a spaced-apart manner must accomplish such suturing and such needle must be moveable.

It is an object of the present invention, to provide a suturing device for use with laproscopic surgery.

It is yet a further object of the present invention, to provide a suturing device, which is articulable over a wide range of movement.

It is still yet a further object of the present invention, to provide a suturing device of elongated proportions, having a very moveable distal end, and a readily controllable proximal end to accomplish suturing in a laproscopic manner.

BRIEF SUMMARY OF THE INVENTION

The present invention comprises of an elongated suturing device, having a proximal or first end comprising a handle, and a distal or a second end comprising an articulable needle shaft.

The handle comprises an elongated generally barrel shaped housing, having a proximalmost end. A threaded shaft is arranged through the proximalmost end, the threaded shaft having a distal end arranged near, the distal end of the handle. The proximal-most end of the threaded shaft has a captor on to permit it to be rotated with respect to the housing permitting relative longitudinal of movement therebetween. The suturing needle is arranged at the distal end of the housing, and comprises a plurality of generally disk-shaped beads. Each of the beads is of the order of less than one-eighth of an inch in diameter. The beads are generally of oval shape in cross-section, and have an upper and a lower planar end, which are non-parallel with respect to one another. A pair of generally rectangular slots extends parallel to each other through each respective bead. The beads are stacked upon one another, one flat surface of each respective bead having a pair of projections thereon, its opposite surface of the bead, having a pair of detents thereon. The column of successive beads have their respective projections and detents intermated so as to provide an interlocking relationship therebetween. The distalmost bead may have a pointed "suture-holding" tip arranged thereon, the tip having a slot by which to hold a suture thread therewithin. An outer sheath is arranged about the proximalmost end of the column of beads comprising the suture needle. The outer sheath is slideable longitudinally with respect to the handle and with respect to the beads.

A rigid connector is arranged between the proximalmost end of the sheath and a tab extending through the outer surface of the handle, to permit longitudinal adjustment of the sheath with respect to the handle-end and to the beads comprising the suture needle.

A thin flat strip of metal, for instanced Nitinol is threaded through one of each of the slots in the column of the beads comprising the suture needle. The first end of that metal strip being attached to the distalmost end of the threaded screw-shaft within the housing. The thin strip of metal extends distally through the column of beads, over the distalmost bead at the distalmost end of the suture device, and back in through the collection of the second slots in each of the column of beads, in a proximal direction. The other end of the metal strip is then anchored to the proximalmost end wall within the handle.

The tension in that steel or Nitinol band arranged through the corresponding slots within the column of beads, may be adjusted, by rotation of the threaded shaft within the handle. Increasing the tension within the steel or Nitinol band by rotation of the threaded shaft will cause the column of beads at its distalmost end, to curve in a "C" or "J" shape, and stiffen. Such action is necessary when making a suture around a body part so as to bring the thread around that body part by the distal end of the suture device.

Movement of the outer sheath distally will help straighten and stiffen the needle by requiring all the beads to be aligned axially therewithin.

Thus, what has been shown is a novel arrangement for a suture device wherein a polarity of stacked disks, each disk having generally non-parallel opposed surfaces which can be lockably engaged and caused to curve in its columnar arrangement, permitting a suturing to take place at its distalmost end.

BRIEF DESCRIPTION OF THE DRAWINGS

The objects and advantages of the present invention will become more apparent when viewed in conjunction with the following drawings, in which:

FIG. 1 is a side elevational view, partly in section, of a suturing device constructed according to the principles of the present invention;

FIG. 2 is a view similar to FIG. 1, showing the suture needle in a curved configuration;

FIG. 3 is a view similar to FIGS. 1 and 2, showing the suture needle in a straight and stiffened configuration;

DESCRIPTION OF THE PREFERRED EMBODIMENTS

Figure 4:
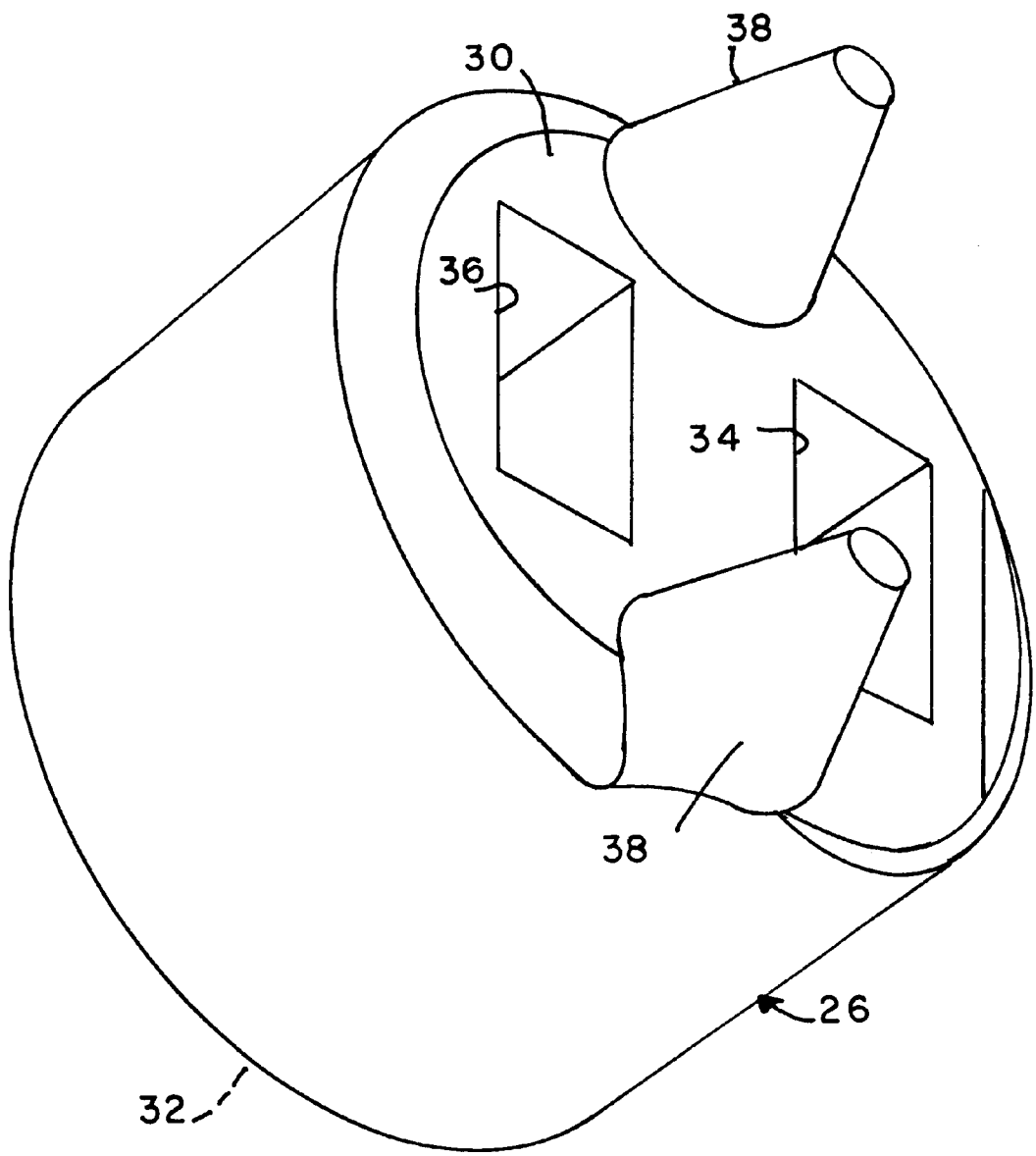
FIG. 4 is an enlarged perspective view of an upper-side of a bead comprising a portion of the suture needle of the present invention.
Figure 5:
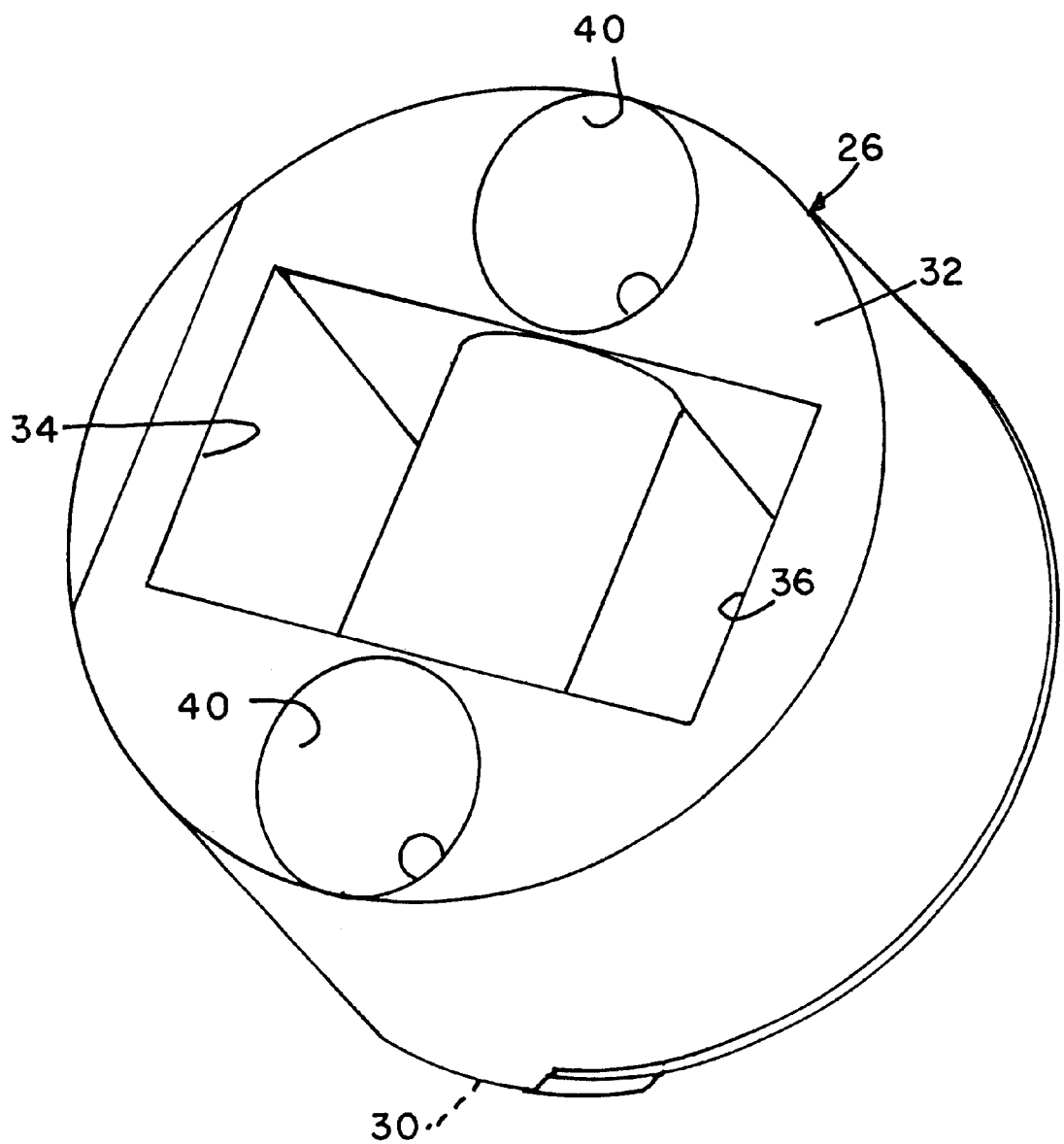
FIG. 5 is a perspective view of a bead showing its lower-most flat surface.
Figure 6:
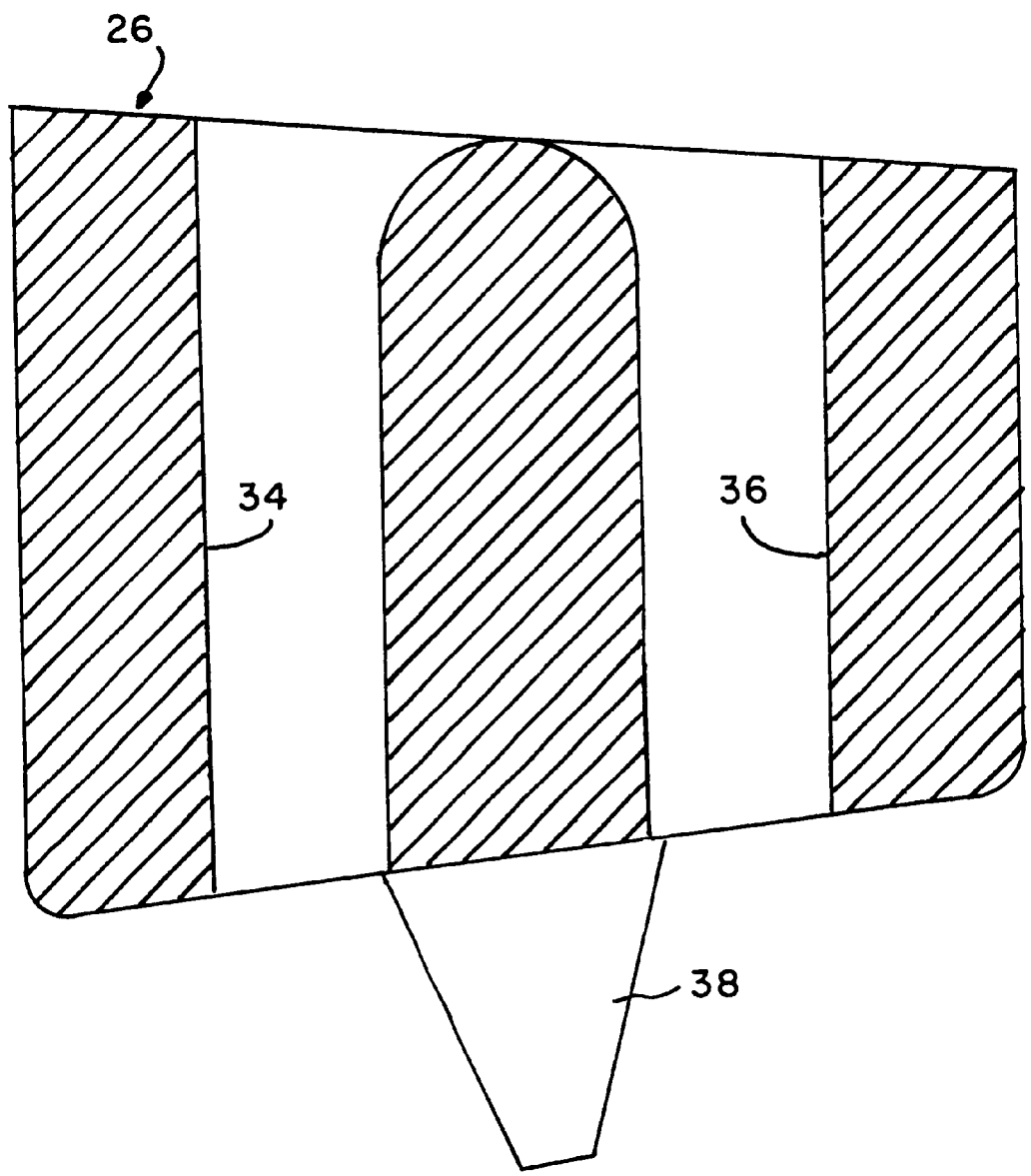
FIG. 6 is a side elevational view, in section, of a bead constructed according to the principles of the present invention.

Referring now to the drawings in detail, and particularly to FIG. 1, there is shown the present invention comprising an elongated suturing device 10, having a proximal or first end comprising a handle 12, and a distal or a second end comprising an articulable needle shaft 14. The handle 12 comprises an elongated generally barrel shaped housing 16, having a closed proximalmost end 18. A threaded shaft 20 is arranged through the proximalmost end 18, the threaded shaft 20 having a proximal end 22 threadedly arranged through the proximal end 18 of the handle 14. The proximalmost end 22 of the threaded shaft 20 has a cap or knob 24 thereon, on to permit it to be rotated with respect to the handle 12, permitting relative longitudinal of movement therebetween. The suturing needle 14 is arranged at the distal end of the handle 12, and comprises a plurality of generally disk-shaped beads 26. Each of the beads 26 is of the order of less than one-eighth of an inch in diameter. Each bead 26 may be of generally of oval shape in cross-section, and have an upper and a lower planar end 30 and 32, as may be seen in FIGS. 4 and 5, which are non-parallel with respect to one another. A pair of generally rectangular slots 34 and 36 extends parallel to each other through each respective bead 26, as may be seen in section in FIG. 6. The beads 26 are stacked upon one another, as may be seen in FIGS. 7 and 8, one flat upper surface 30 of each respective bead 26 having a pair of projections 38 thereon, its opposite surface 32 of the bead 26, having a pair of detents 40 thereon. The column of successive beads 26 have their respective projections 38 and detents 40 intermated, so as to provide an elongated, articulable, interlocking relationship therebetween. The distalmost bead 26, as shown in FIGS. 1, 2 and 3, may have a pointed "suture-holding" tip 42 arranged thereon, the tip 42 having a slot by which to hold a suture thread (not shown) therewithin. A flexible outer sheath 46, is arranged about the proximalmost end of the column of beads 26 comprising the suture needle 14. The outer sheath 46 is slideable longitudinally with respect to the handle 12 and with respect to the beads 26.

A rigid connector 50 is arranged between the proximalmost end of the sheath 46 and a tab 52 extending through the outer surface of the handle 12, to permit longitudinal adjustment of the sheath 46 with respect to the handle-end and to the beads 26 comprising the suture needle 14.

A thin flat strip of metal 56, for instance, steel or Nitinol, is threaded through one of each of the slots in the column of the beads 26 comprising the suture needle 14. The first end of that metal strip 56 being attached to the distalmost end of the threaded screw shaft 20 within the housing 16. The thin strip of metal 56 extends distally through the column of beads 26, over the distalmost bead 26 at the distalmost end of the suture device 10, and back in through the collection of the second slots in each of the column of beads 26, in a proximal direction. The other end of the metal strip 56 is then anchored to the proximalmost end wall 58 within the handle 12, as may be seen in FIGS. 1, 2 and 3.

Figure 7:
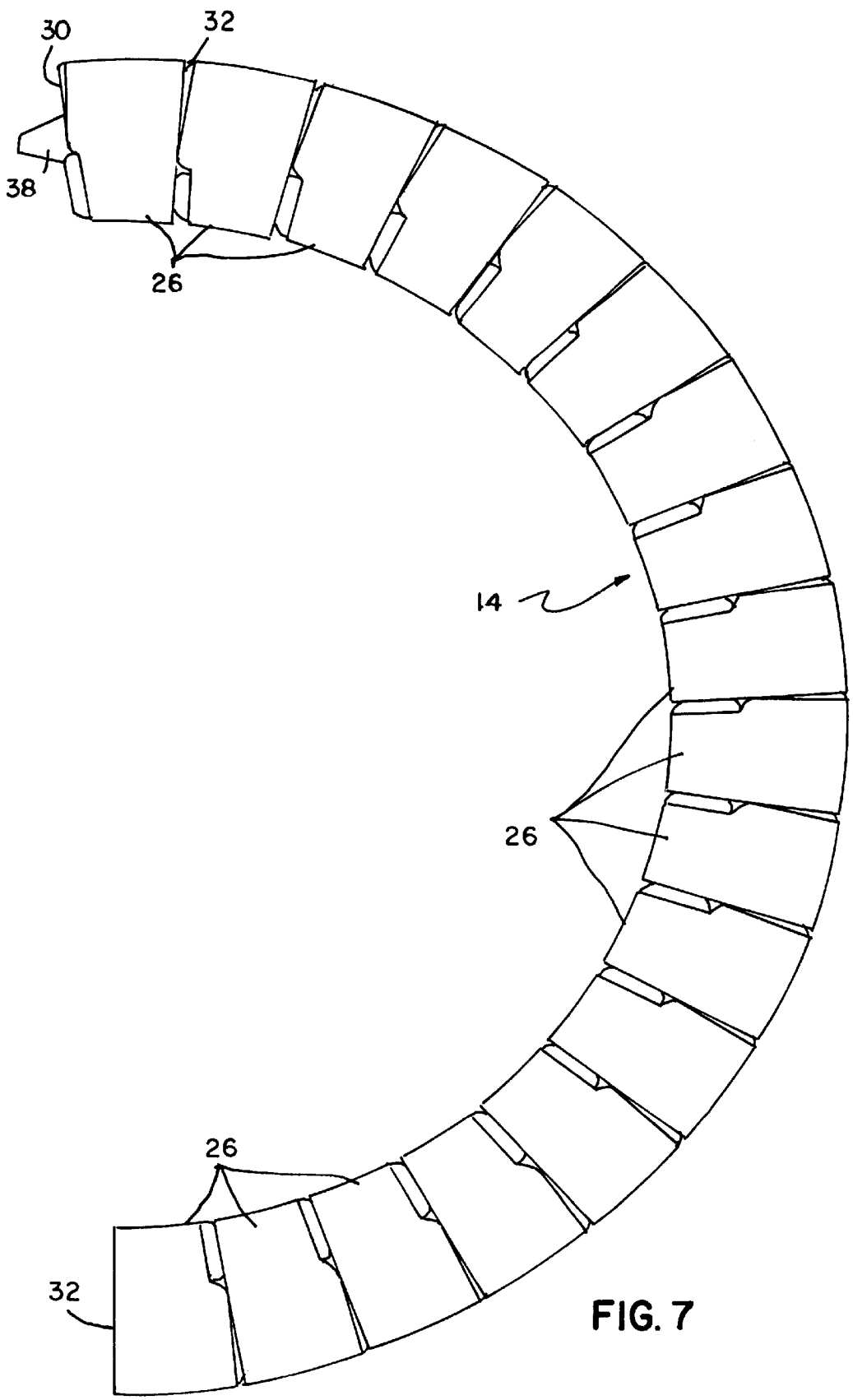
FIG. 7 is a side elevational view of a plurality of beads shown in a generally U-shaped configuration.
Figure 8:
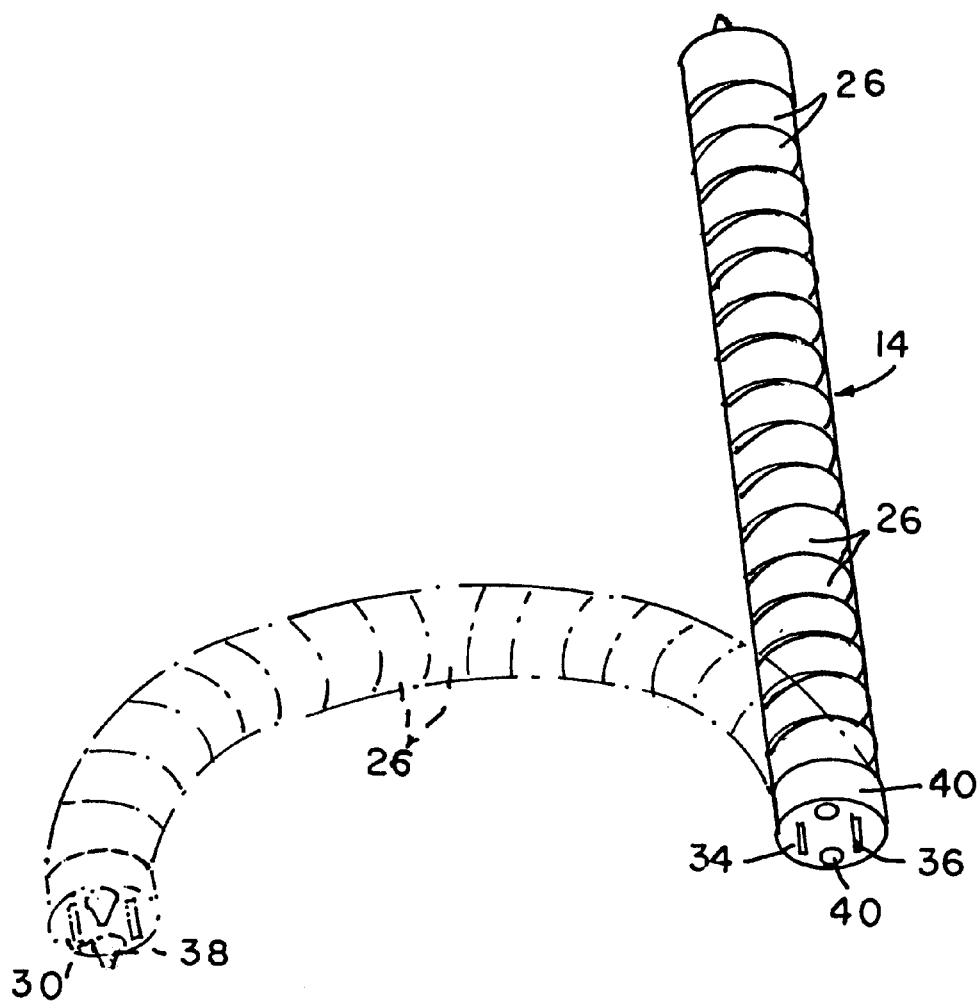
FIG. 8 is a perspective view of a column of beads shown in its linear configuration and in phantom in a curvilinear figuration.

The tension in that steel or Nitinol band 56 arranged through the corresponding slots 30 and 32 within the column of beads 26 may be adjusted, by rotation of the threaded shaft 20 within the handle 12. Increasing the tension within the steel or Nitinol band 56, by rotation of the threaded shaft 20, will cause the column of beads 26 at its distalmost end, to curve in a "C" or "J" shape, and stiffen, as is shown in FIGS. 2, 7 and 8. Such action is necessary when making a suture around a body part so as to bring the thread around that body part by the distal end of the suture device 10.

Movement of the outer sheath 46 distally will help straighten and stiffen the needle 14, by requiring all the beads 26 to be aligned axially therewithin, as shown in FIG. 3.

Thus, what has been shown is a novel arrangement for a suture device wherein a polarity of stacked disk-like beads, each bead having generally non-parallel opposed surfaces 30 and 32, which can be lockably engaged and caused to curve in its columnar arrangement, permitting a suturing to take place at its distalmost end.

What is claimed is:

1. A method of suturing a body part by the use of an elongated articulable suture device comprising the steps of:

providing a handle having a proximal end and a distal end with a suture needle thereat;

threading a tensionable member through said suture needle from a proximal to distal path and back again through a distal to proximal path, one end of said tensionable member being fixed to said handle, and a second end of said tensionable member being attached to a tension adjusting member;

placing a suture thread in a holder in said distalmost end of said suture needle; and suturing a body part with said suture device.

2. The method as recited in claim 1, including the step of:

adjusting said tensioning member to cause articulation in said suture needle.

3. The method as recited in claim 1, including the step of:

arranging a flexible outer sheath said about said suture needle to effect a further articulation of said suture needle.

4. The method as recited in claim 1, wherein said suture needle is comprised of a plurality of disks arranged in a stack.

5. The method as recited in claim 4, wherein each of said disks have a pair of flat opposed surfaces.

6. The method as recited in claim 5, wherein each of said flat opposed surfaces of said beads have interlocking mating projections or detents thereon, to permit arranging said beads in a columnar manner.

7. The method as recited in claim 5, wherein each of said beads has a pair of slots extending therethrough, to permit the passage of said tensioning member therewithin.

* * * * *